United States Patent [19]

Dolhyj et al.

[11] 4,097,501

[45] Jun. 27, 1978

[54] USE OF COATED CATALYSTS IN THE PREPARATION OF MALEIC ANHYDRIDE

[75] Inventors: Serge R. Dolhyj, Parma; Ernest C. Milberger, Solon; Sandra R. Evans, Cleveland, all of Ohio

[73] Assignee: The Standard Oil Company, Cleveland, Ohio

[21] Appl. No.: 687,827

[22] Filed: May 19, 1976

[51] Int. Cl.² ............................................. C07D 307/60
[52] U.S. Cl. ............................... 260/346.74; 252/437; 252/461; 252/467; 252/469; 252/477 R
[58] Field of Search ......................... 260/346.8, 346.74

[56] References Cited

U.S. PATENT DOCUMENTS

| | | | |
|---|---|---|---|
| 2,954,385 | 9/1960 | Burney et al. | 260/346.4 |
| 3,464,930 | 9/1969 | Friedrichsen et al. | 252/469 |

Primary Examiner—John M. Ford
Assistant Examiner—Bernard Dentz
Attorney, Agent, or Firm—Gwenetta Douglas Hill; Herbert D. Knudsen; Larry W. Evans

[57] ABSTRACT

Very desirable temperature control and selectivity are obtained in the oxidation of benzene to maleic anhydride using an oxidation catalyst of an essentially inert support of at least 20 microns containing on its outer surface a coating of a catalytically active oxide material or a catalytically active oxide material and an oxide support.

9 Claims, No Drawings

USE OF COATED CATALYSTS IN THE PREPARATION OF MALEIC ANHYDRIDE

BACKGROUND OF THE INVENTION

There are a large number of catalysts known to be effective in the oxidation of benzene to maleic anhydride in a fixed-bed reactor. The present invention is not a new catalyst but a method of adapting the known catalysts to an improved process for preparing maleic anhydride.

In the oxidation of benzene to maleic anhydride, very significant problems of heat generation are encountered because of the exothermic nature of the reaction. The present invention is directed toward the solution of this problem by a more economically acceptable technique.

The invention is not the nature of the active catalytic material nor the nature of the particular support material, but the invention is the specific combination of these two aspects of the catalyst in such manner that a catalyst which is especially desirable for the oxidation of benzene to maleic anhydride is obtained.

Difficulties with a fixed bed exothermic reaction are well known. The basic problem is that the heat generated cannot be dissipated by normal heat transfer techniques. Accordingly, the temperature of the reaction cannot be controlled. Also, "hot spots" in the reaction develop where no useful reaction occurs. The present invention is designed to alleviate these problems by the use of coated catalysts that can be conveniently prepared.

SUMMARY OF THE INVENTION

It has now been discovered in the process for the preparation of maleic anhydride by the reaction of benzene with air, and optionally steam, in the presence of an oxidation catalyst which is useful for the reaction in a fixed-bed reactor, the improvement comprising using a catalyst consisting of (1) an essentially inert support of at least about 20 microns in diameter, said support having an outer surface, and (2) a coating consisting essentially of (a) a catalytically active oxide material or (ii) a catalytically active oxide material and an oxide support material on the outer surface of the inert support which strongly adheres to the outer surface of the inert support.

The strongly exothermic reaction in the oxidation of benzene to maleic anhydride is more easily controlled by the process of the present invention. These catalysts are conveniently prepared and make it possible to conduct this strongly exothermic reaction in a fixed-bed reactor with greater ease.

The central feature of the invention is the catalyst employed. The components of the catalyst are not new and may be selected from a wide variety of materials that are known in the art. As noted, the catalyst of the present invention contains two separate parts--an essentially inert support and an active catalytic material.

The essentially inert support may be selected from a wide choice of materials available in the art. This support material is massive and must have a diameter of at least about 20 microns. Preferred supports have a diameter of about 0.06 centimeters to about 1.8 centimeters, but there is no limitation on the size of the support material.

The support material must be at least partially porous. By this is meant the support material must be susceptible to the penetration of liquid. Preferred support materials are capable of absorbing at least about 1% by weight of water based upon the weight of the support.

In a reactor one of the important variables is the pressure drop. The present invention can be utilized to minimize the pressure drop by the use of spherical catalysts. These spherical catalysts can be prepared by using a spherical support material and distributing the active catalytic material evenly on the outer surface of the support.

The inert support may be any material that is not active in the oxidation reaction. Suitable examples of essentially inert support materials include: Alundum, silica, alumina, alumina-silica, silicon carbide, titania and zirconia. Especially preferred among these supports are Alundum, silica, alumina and alumina-silica.

The second component of the catalyst employed in the present invention is the catalytically active material. The term "catalytic material" means the active catalytic ingredients optionally containing a support material, such as silica, dispersed throughout the active ingredients.

Essentially any catalytic material may be used in the catalysts of the invention. Even though the class of catalysts is essentially unlimited, experience has shown that the present invention is especially adaptable to the use of catalysts containing catalytically active metal oxide catalysts or catalyst precursors that are converted to oxide catalysts are preferred.

In the present invention the preferred catalysts contain in the active catalytic component, oxides of alkali metals, alkaline earth metals, V, Cr, Mo, W, Mn, Fe, Co, Ni, Cu, Zn, In, Te, Sn, Sb, Bi, Ag, U, As, and optionally an oxide of phosphorus. Preferred among these catalysts are those which contain at least the oxides of molybdenum and vanadium. Also preferred are those catalysts which contain active components of the catalyst including at least the oxides of phosphorus, tin, vanadium and molybdenum.

The catalysts may contain essentially any proportions of support and catalytically active material. The limits on this relationship are only set by the relative ability of the catalyst and support material to accommodate each other. Preferred catalysts contain about 10 to about 100 percent by weight of catalytically active material based on the weight of the support.

One very intriguing aspect of the present invention is the possibility of coating the catalyst with two or more specific catalysts. Using the proper reactions and selective catalysts, two reactions could be conducted simultaneously or alternately to increase the utility of the reactor.

Now that the particular components of the catalyst have been described, the preparation of these catalysts can be considered. The preparation of these catalysts can be accomplished by various techniques. The basic method of preparing these catalysts is to partially wet the support material with a liquid. The support cannot be wet on the outside surface of the total mass. It should be dry to the touch. If the support is wet, then the active catalytic material will agglomerate into separated aggregates when coating of the support is attempted. These partially wet supports are then contacted with a powder of the catalytically active material and the mixture is gently agitated until the catalyst is formed.

The gentle agitation is most conveniently conducted by placing the partially wet support in a rotating drum and adding the active catalytic material until none is taken up by the support. This is very economically done.

The liquid used to wet the support may include inorganic or organic liquids and is essentially dependent upon the type of catalytically active material employed. The liquid and the catalytically active material must have a relatively high degree of attraction for each other. For example, if a hydrophylic catalytically active material is used, water may be used to wet the support. On the other hand if a hydrophobic catalytically active material is used, an organic solvent such as petroleum ether could be used. Water is the preferred liquid.

More specifically, the catalyst of the invention is prepared by (1) contacting an essentially inert support of at least about 20 microns in diameter with an excess of liquid in such manner that the liquid is absorbed by the support to produce a wet support, (2) drying said wet support to produce a partially wet support, said partially wet support is defined as one that does not have the appearance of liquid on the outer surface of the support, but has at least some liquid absorbed on the support, (3) contacting the partially wet support with a powder consisting essentially of (a) a catalytically active oxide material having a particle size of less than about 500 microns, or (b) a catalytically active oxide material having a particle size of less than about 500 microns and an oxide support material, and gently agitating the mixture of partially-wet support and catalytically active oxide material to produce an inert support having a strongly adherent coating of (i) catalytically active oxide material or (ii) a catalytically active oxide material and an oxide support material.

Alternately, the catalyst may be prepared by contacting an essentially inert support of at least 20 microns in diameter with a measured amount of liquid to produce a partially wet support being one that does not have the appearance of liquid on the outer surface of the support, but has at least some liquid absorbed on the support, (1) contacting said partially wet support with a powder of (a) a catalytically active oxide material or (b) a catalytically active oxide material and an oxide support material having a particle size of less than about 500 microns, and (2) gently agitating the mixture of partially wet support and (a) catalytically active oxide material or (b) catalytically active oxide material and an oxide support material to produce an inert support having a strongly adherent coating of said material.

After the above steps have been taken in the catalyst preparation, other drying and activation steps can be used to produce the desired catalysts. These steps are known in the art and are not significantly altered by the present invention.

The present invention employs a catalyst that combines the catalytically active material and inert support material in a manner that provides an especially effective catalyst for the strongly exothermic reaction occurring in the oxidation of benzene to maleic anhydride.

The catalysts prepared by the process of the invention consist of the inert support and a strongly-adhering coat of the active catalytic ingredients on the outer surface of the support. The catalytic ingredients are maintained on the surface of the support, and there is essentially no impregnation of the active ingredients into the inert support. Thus, the catalysts of the invention are sharply contrasted with those catalyst techniques that impregnate an inert support with an active catalyst by contacting the support with a liquid or slurry of active ingredients.

The coated catalysts of the present invention are used in the oxidation of benzene to maleic anhydride. The oxidation is a known reaction, and the reaction conditions, feed ratios and design of the reaction system is not materially changed from that of the art. Broadly, the ratio of molecular oxygen to benzene could be as low as about four moles per mole of benzene, but there is no theoretical upper limit. Normally, the molecular oxygen is added as air, and the air/benzene ratio usually ranges from about 40 to 130 or more.

SPECIFIC EMBODIMENTS

Comparative Example A and Example 1

Preparation of Maleic Anhydride using Coated Catalysts of the Invention Compared with Art Preparation.

Active catalytic material having the formula 30% $V_2MoO_x \cdot Mo°_{0.02}$ + 70% Alundum was prepared by slurrying 33.20 g. of vanadium pentoxide and 26.27 g. of molybdenum trioxide in about 500 cc. of distilled water. To this stirred slurry was added 0.35 g. of molybdenum powder. The slurry was heated under stirring and refluxed for 2 hours, during which time the color changed to deep blue-black. The catalyst was evaporated to a paste and dried in an oven overnight at a temperature of 110° C. and activated for 2 hours at 427° C. in a muffle furnace.

In Example 1, the black powder obtained was coated onto an Alundum support (10-30 mesh size) by the following procedure: 30 grams of Norton SA 5223 Alundum was wetted with 2.4 grams of distilled water by rolling in a glass jar. The material was free-flowing and outwardly dry. To this material, in a rotating jar, was added 12.86 grams of the dried black powder in several incremental additions. The powder was evenly coated onto the surface of the Alundum.

In Comparative Example A, the identical set of active materials were deposited on Norton SA 5223 Alundum particles by impregnation at 30% active level by evaporation of active slurry in the presence of Alundum.

The impregnated and coated catalysts were tested in parallel reactions to produce maleic anhydride from benzene in a 40 cc. fixed-bed reactor using semi-commercial size 0.32 cm. spherical catalyst particles. The reactor had a 1.91 cm. outside diameter with 0.25 cm. wall thickness. Benzene was fed in this reactor using a Milton Roy minipump (16/160 ml model) in the ratio 1 benzene/60 air at approximately 1 second contact time.

The exotherm was recorded for each of the reactions by recording the bath temperature and recording the temperature in the center of the reactor using a thermowell.

The results are stated in terms as follows:

$$\text{Single Pass Yield} = \frac{\text{Moles of Maleic Anhydride Formed} \times 100}{\text{Moles of Benzene Fed}}$$

$$\text{Total Conversion} = \frac{\text{Moles of Benzene Reacted} \times 100}{\text{Moles of Benzene Fed}}$$

$$\text{Selectivity} = \frac{\text{Single Pass Yield} \times 100}{\text{Total Conversion}}$$

The experimental results are shown in TABLE I.

TABLE I

Preparation of Maleic Anhydride Using Coated Catalyst
30% $V_2MoO_x \cdot Mo°_{0.02}$ + 70% Alundum compared with Art Preparation

| Example | Form of Catalyst | Temp. ° C. | | | Results, % | |
|---|---|---|---|---|---|---|
| | | Bath | Thermowell | Exotherm | Single Pass Yield | Selectivity |
| Comp. A | Impregnated | 425 | 449 | 24 | 23.0 | 38.2 |
| 1 | Coated | 425 | 437 | 12 | 31.2 | 48.4 |

Thus, it can be seen from the above parallel experiments that the coated catalyst showed appreciably lower exotherms, better selectivity, and higher per pass conversion to maleic anhydride.

Examples 2 and 3

Effect of Catalyst Coating and Process Steam

A portion of the catalyst prepared in accordance with Example 1 was reacted in the absence of steam in a 20 cc. fixed-bed reactor having a 1.27 cm. outside diameter stainless steel tubing. Benzene was pumped using Sage tubing pump (model 375A) evaporated in heated compartment (about 200° C.) by passage through 0.05 cm. inside diameter capillary tubing at 1 benzene/60 air ratio at approximately 1 second contact time.

Subsequently, the catalyst prepared in Example 1 was reacted in the presence of steam in the ratio 1 benzene/60 air/40 water at a contact time of 0.6 seconds. Experimental results appear in TABLE II.

TABLE II

Effect of Catalyst Coating and Process Steam

| Example | Temp. ° C | | | Ratio | | | Results, % | |
|---|---|---|---|---|---|---|---|---|
| | Bath | Thermowell | Exotherm | Benzene | Air | $H_2O$ | Maleic Anhydride | Selectivity |
| 2 | 478 | 487 | 9 | 1 | 60 | 0 | 35.6 | 39.9 |
| 3 | 476 | 487 | 11 | 1 | 60 | 40 | 41.0 | 47.0 |

In the same manner as described in the examples above, other reactant ratios can be employed; for example benzene, air and steam in a ratio of 1/14/55 could be fed over a catalyst at temperatures of 385° to 450° C. or 1/10/90 at temperatures of 470° to 510° C. to obtain desirable yields of maleic anhydride.

Also in the same manner as shown for the catalysts above, other catalysts may be employed, such as 30% $V_2MoSn_{0.1}O_x \cdot Mo°_{0.02}$ + 70% Alundum or 10% ($10V_2MoO_x \cdot Mo°_{0.02}$ + $90TiO_2$) + 90% Alundum.

The reaction temperature may vary widely but is usually within the range of about 200° to about 600° C., with temperatures of about 300° to 500° C. being preferred. The reaction can be run at atmospheric, superatmospheric, or subatmospheric pressure. The catalysts of the invention are most suited for fixed-bed operation, but using small support particles, it is also possible to conduct the reaction in a fluid-bed reactor.

The catalysts of the invention produce especially desirable yields of maleic anhydride and useful by-products. In the past, the exotherm created in the reactor caused loss of control, but now with the catalysts of the invention, an even temperature is easily maintained without use of special diluents or low reactant feed rates.

We claim:

1. In a process for the preparation of maleic anhydride by the reaction of benzene with air, and optionally steam, in the presence of an oxide catalyst which is useful in a fixed-bed reactor, the improvement comprising:

using a catalyst consisting of
(a) an essentially inert, at least partially porous support having a particle size of at least 20 microns, wherein said support has an outer surface, said support being selected from the group consisting of silica, alumina, silicon carbide, alumina-silica, titania and zirconia; and
(b) a coating consisting essentially of a catalytically active oxide material on said outer surface of said support which strongly adheres to said outer surface of said support, wherein said catalytically active oxide material contains at least an oxide of vanadium or an oxide of molybdenum, and wherein said catalyst is prepared by (1) contacting the support with a liquid to produce a partially wet support, said partially wet support being one that does not have the appearance of having liquid on the outer surface of said support; and (2) contacting said partially wet support with a powder of a catalytically active material to produce a support having a strongly adherent coating of said catalytically active material on the outer surface of said support.

2. The process of claim 1 wherein the coating is about 10 to about 100 percent by weight of the inert support.

3. The process of claim 1 wherein said inert support is capable of absorbing at least 1% by weight water based upon the weight of the support, but does not have the appearance of having water on the outer surface of the support.

4. The process of claim 1 wherein the active catalytic oxide material contains at least the oxides of V and Mo.

5. The process of claim 1 wherein the catalytically active oxide material additionally contains one or more members of the group consisting of oxides of alkali metals, alkaline earth metals, chromium, tungsten, manganese, iron, cobalt, nickel, copper, zinc, indium, tellurium, antimony, tin, bismuth, silver, arsenic and phosphorus.

6. The process of claim 1 wherein the active catalytic oxide material contains at least the oxides of Mo, V, Sn, and P.

7. The process of claim 5 wherein the catalytically active oxide material does not contain an oxide of phosphorus.

8. The process of claim 1 wherein the reaction is conducted in the presence of steam.

9. The process of claim 1 wherein the inert support is essentially spherical.

* * * * *

UNITED STATES PATENT AND TRADEMARK OFFICE
CERTIFICATE OF CORRECTION

PATENT NO. : 4,097,501
DATED : June 27, 1978
INVENTOR(S) : Serge R. Dolhyj et al It is certified that error appears in the above-identified patent and that said Letters Patent are hereby corrected as shown below:

Column 6, Line 57, after "silver" add --uranium--

Signed and Sealed this

Twentieth Day of March 1979

[SEAL]

Attest:

RUTH C. MASON
Attesting Officer

DONALD W. BANNER
Commissioner of Patents and Trademarks